(12) United States Patent
Kim et al.

(10) Patent No.: US 10,278,652 B2
(45) Date of Patent: May 7, 2019

(54) DISPLAY APPARATUS

(71) Applicant: SAMSUNG DISPLAY CO., LTD., Yongin-si, Gyeonggi-do (KR)

(72) Inventors: Young Chan Kim, Incheon (KR); Katsumasa Yoshii, Suwon-si (KR)

(73) Assignee: Samsung Display Co., Ltd., Yongin-Si, Gyeonggi-do (KR)

( * ) Notice: Subject to any disclaimer, the term of this patent is extended or adjusted under 35 U.S.C. 154(b) by 0 days.

(21) Appl. No.: 15/013,327

(22) Filed: Feb. 2, 2016

(65) Prior Publication Data

US 2016/0361031 A1 Dec. 15, 2016

(30) Foreign Application Priority Data

Jun. 10, 2015 (KR) ........................ 10-2015-0081989

(51) Int. Cl.
*A61B 5/00* (2006.01)
*H01L 27/32* (2006.01)
*H01L 51/52* (2006.01)
*A61B 5/024* (2006.01)

(52) U.S. Cl.
CPC .......... *A61B 5/7445* (2013.01); *A61B 5/0059* (2013.01); *A61B 5/024* (2013.01); *A61B 5/6802* (2013.01); *H01L 27/3227* (2013.01); *H01L 51/5271* (2013.01); *A61B 5/681* (2013.01); *A61B 5/6803* (2013.01); *A61B 5/6804* (2013.01); *A61B 2562/0238* (2013.01); *A61B 2562/185* (2013.01); *H01L 51/5284* (2013.01); *H01L 2251/5323* (2013.01)

(58) Field of Classification Search
CPC ..... A61B 5/7445; A61B 5/0059; A61B 5/024; A61B 5/6802; A61B 5/6803; A61B 5/6804; A61B 5/681; A61B 2562/0238; A61B 2562/185; H01L 27/3227; H01L 51/5271; H01L 51/5284; H01L 2251/5323
See application file for complete search history.

(56) References Cited

U.S. PATENT DOCUMENTS

| | | |
|---|---|---|
| 2008/0018242 A1 | 1/2008 | Shen et al. |
| 2013/0127790 A1 | 5/2013 | Wassvik |
| 2014/0061617 A1 | 3/2014 | So et al. |
| 2014/0320553 A1 | 10/2014 | Eom et al. |

FOREIGN PATENT DOCUMENTS

| | | |
|---|---|---|
| CN | 103107172 A | 5/2013 |
| KR | 10-2012-0065653 A | 6/2012 |

*Primary Examiner* — Deborah L Malamud
(74) *Attorney, Agent, or Firm* — Lee & Morse, P.C.

(57) ABSTRACT

A display device includes a sensor, a transparent substrate, and a plurality of light emitters adjacent a first side the transparent substrate. The light emitters emit light in a first direction and a second direction opposing the first direction. The sensor senses reflected light, which is emitted through a second side of the transparent substrate and received by the sensor after being reflected from a location outside the display device.

21 Claims, 8 Drawing Sheets

DISPLAY APPARATUS

CROSS-REFERENCE TO RELATED APPLICATION

Korean Patent Application No. 10-2015-0081989, filed on Jun. 10, 2015, and entitled, "Display Apparatus," is incorporated by reference herein in its entirety.

BACKGROUND

1. Field

One or more embodiments described herein relate to a display apparatus.

2. Description of the Related Art

One recent development in consumer electronics is the advent of wearable devices in the form of glasses, a watch, or clothing. A wearable device may include a display, communication module, and control device for controlling the communication module. The display may output user-desired information. Also, the device may monitor the status of the wearer. However, when the display and a sensor for monitoring the status of the wearer are provided separately, the overall thickness of the device may increase, which may be uncomfortable to the wearer.

SUMMARY

In accordance with one or more embodiments, a display device includes a sensor; a transparent substrate; and a plurality of light emitters at a first side of the transparent substrate; wherein the light emitters are to emit light in a first direction and a second direction opposing the first direction, and wherein the sensor is to sense reflected light emitted through a second side of the transparent substrate and received by the sensor after being reflected from a location outside the display device. The display device may include a reflector to at least partially reflect the light emitted in the first direction to the second direction. The reflector may include a reflective surface that covers a portion of a light emission surface of one or more of the light emitters, the reflective surface having a concave shape toward the first direction.

The display device may include a cathode between the reflector and one or more of the light emitters and connected to the one or more light emitters, wherein a part of the cathode is curved in the first direction along the reflective surface of the reflector. The reflective surface may include a first reflective surface having a first curvature center and a first curvature and a second reflective surface having a second curvature center and a second curvature, and at least two of the first curvature center, the second curvature center, the first curvature, and the second curvature are different.

The reflector may include a first reflection portion and a second reflection portion, and the first reflection portion and the second reflection portion cover different edges of one of the light emitters. The light emitters may include first light emitters to emit light of a first color, second light emitters to emit light of a second color, and third light emitters to emit light of a third color, and the reflector may partially covers at least one of the first, second, or third light emitters.

The display device may include a light blocking layer between the transparent substrate and one or more of the light emitters, wherein an opening that at least partially overlaps the reflector and through which light is to be transmitted is in the light blocking layer. The sensor may include a first sensor and a second sensor, and the reflector may overlap a space between the first and second sensors. The sensor may be at the first side of the transparent substrate, a protection layer may cover the sensor, and the light emitters may be on the protection layer. The sensor may be at the second side of the transparent substrate, and a protection layer may cover the sensor.

The display device may include a reflective plate covering the second side of the transparent substrate and including an opening in a center of the reflective plate; a reflective space between the reflective plate and the transparent substrate; and a light collector in the reflective space and substantially aligned with the opening of the reflective plate. The reflective plate may gradually incline from an edge of the reflective plate toward the second direction closer to the center where the opening is formed, and a thickness of the reflective space may gradually increase from an edge of the second side toward a center of the second side. The sensor may be adjacent to the opening.

The display device may include a shield to selectively shut off or open the opening. The reflective space may include light-transmissive material. The sensor may be in the reflective space and substantially aligned with the opening.

The light emitters may include front light emitters to emit light in the first direction and bottom light emitters to emit light in the second direction, and the bottom emitters may be adjacent to an edge of the transparent substrate. The display device may include a shield covering the bottom light emitters in the first direction. The sensor may be adjacent to the edge of the second side of the display substrate and does not overlap the bottom light emitters. An amount of light to be emitted in the second direction may be in a range of about 5% to about 25% of an amount of light to be emitted in the first direction.

BRIEF DESCRIPTION OF THE DRAWINGS

Features will become apparent to those of skill in the art by describing in detail exemplary embodiments with reference to the attached drawings in which.

DETAILED DESCRIPTION

Figure 1:
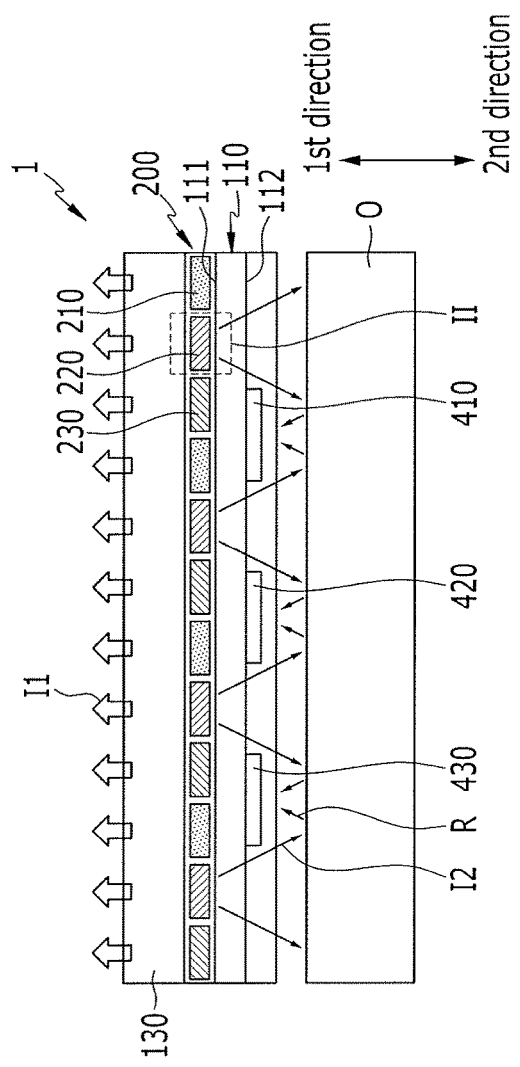
FIG. 1 illustrates an embodiment of a display device.

Example embodiments are described more fully hereinafter with reference to the accompanying drawings; however, they may be embodied in different forms and should not be construed as limited to the embodiments set forth herein. Rather, these embodiments are provided so that this disclosure will be thorough and complete, and will fully convey exemplary implementations to those skilled in the art. The embodiments may be combined to form additional embodiments.

It will also be understood that when a layer or element is referred to as being "on" another layer or substrate, it can be directly on the other layer or substrate, or intervening layers may also be present. Further, it will be understood that when a layer is referred to as being "under" another layer, it can be directly under, and one or more intervening layers may also be present. In addition, it will also be understood that when a layer is referred to as being "between" two layers, it can be the only layer between the two layers, or one or more intervening layers may also be present. Like reference numerals refer to like elements throughout.

When an element is referred to as being "connected" or "coupled" to another element, it can be directly connected or coupled to the another element or be indirectly connected or coupled to the another element with one or more intervening elements interposed therebetween. In addition, when an element is referred to as "including" a component, this indicates that the element may further include another component instead of excluding another component unless there is different disclosure.

Figure 2:
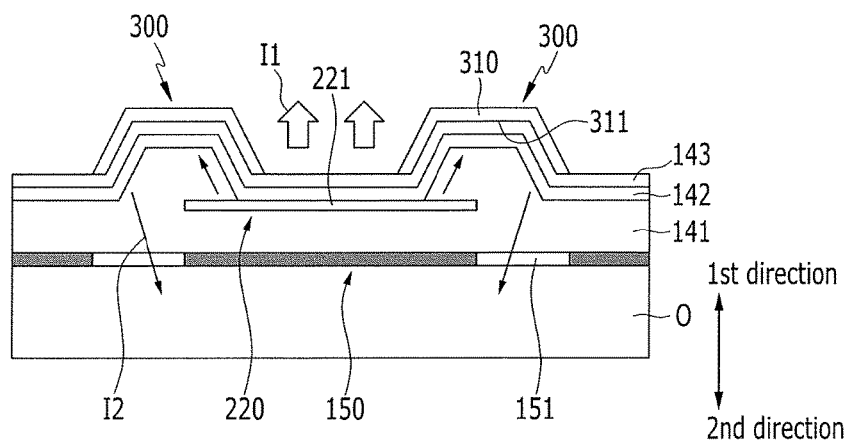
FIG. 2 illustrates an enlarged view of portion II in FIG. 1.

FIG. 1 is a cross-sectional view of an embodiment of a display device 1, and FIG. 2 is an enlarged view of portion II in FIG. 1. The display device 1 is installed in a wearable device (e.g., a watch or clothing) and emits light for displaying an image at one side of the wearable device and/or emits light for sensing body status information of a user at another side of the wearable device.

Referring to FIG. 1, the display device 1 includes a transparent substrate 110, a plurality of light emitting elements 210, 220, and 230, and light receiving sensors 410, 420, and 430. The transparent substrate 110 has a first side 111, and a second surface opposite to the first side 111. An insulating layer made of an insulating material may be formed in or on the transparent substrate 110.

The transparent substrate 110 includes a transmissive material and a flexible material such as polyimide, polyethylene terephthalate, polyethylene naphthalate (PEN), polycarbonate, polyethersulfone (PES). The transmissive material and the flexible material may be different or the same material.

The light emitting elements 210, 220, and 230 are at the first side 111 of the transparent substrate 110, and emit light in a first direction where the first side 111 faces. For example, the light emitting elements 210, 220, and 230 may include organic light emitting diodes (OLEDs). A first light emitting element 210 may emit light of a first color, a second light emitting element 220 may emit light of a second color, and a third light emitting element 230 may emit light of a third color. The first color, the second color, and the third color may be, for example, red R, green G, and blue B, respectively.

The first light-emitting device 210, the second light-emitting device 220 and the third light-emitting device 230 are sequentially arranged in an array and form one pixel to emit light to form an image corresponding to image signals.

A passivation layer 130 may be on the light emitting elements 210, 220, and 230 to cover the transparent substrate 110 and the light emitting elements 210, 220, and 230.

A plurality of light-receiving sensors 410, 420, and 430 are at the second side 112 of the transparent substrate 110. The light-receiving sensors 410, 420, and 430 may include, for example, a photoresistor and/or a light sensing element for receiving light and generating a sense signal from the received light like the photoresistor.

The light emitting elements 210, 220, and 230 of the display device 1 emits light toward the first direction. In this case, light emission surfaces of the light emitting elements 210, 220, and 230 may be formed to face the first direction.

In addition, light emitted from parts 220 of the light emitting elements 210, 220, and 230 (e.g., from the second light emitting element 220) may be partially emitted in a second direction, e.g., in a direction where the second side 112 of the transparent substrate 110 faces opposite to the first direction.

FIG. 2 illustrates an embodiment of a second light-emitting device 220 corresponding to portion II in FIG. 1. Referring to FIG. 2, the display device 1 in portion II includes an organic layer 131, a cathode 142, an insulating layer 143, a light blocking layer 150, and a reflection portion 300.

The organic layer 141 is at the first side 111 of the transparent substrate 110 and includes one or more organic materials. The second light emitting elements 220 may be on an upper surface of the organic layer 141, and an anode electrode connected with the second light emitting element 220 may be formed on the organic layer 141.

The cathode 142 is at the side of a light emission surface 221 of the second light-emitting device 220, and thus is connected with the second light-emitting device 220 and disposed at an upper side of the organic layer 141.

The insulating layer 143 includes an insulating material that covers an upper surface of the cathode 142. The organic layer 141, the cathode 142, and the insulating layer 143 may be made of a light transmissive material.

The reflection portion 300 reflects a portion of light emitted from the second light-emitting device 220 in the second direction, and includes a reflective member 310 that includes a highly-reflective metal material.

A concave reflective surface 311 is formed toward the first direction on the reflective member 310, and the reflective surface 311 partially covers the light emitting surface 221 of the second light-emitting device 220.

In FIG. 2, the reflective surface 311 is illustrated as a plurality of planes arranged with predetermined angles, but the reflective surface 311 may be formed as a single curved surface in another embodiment. In this case, a pair of reflection portions 300 may overlap respective edges of the light emitting surface 221 of the second light-emitting device 220.

Light is emitted from an area between the reflection portions 300 among the light emitting surface 221 of the second light-emitting device 220, e.g., light is emitted from an area not covered by the reflection portions 300. This light corresponds to front light I1 emitted in the first direction. Light may be emitted from an area covered by the reflection portion 300 among the reflective surface 2110 of the second light-emitting device 220. This light may correspond to bottom light I2 which is emitted toward the reflection portion 300, reflected from the reflective surface 311, emitted in the second direction.

Parts of the cathode 142 and the insulating layer 143 may be covered by the reflection portions 300. These parts of the cathode 42 and the insulating layer 143 may, for example, be curved in the first direction along the reflective surface 311.

The light blocking layer 150 is between the first side 111 of the transparent substrate 110 and the organic layer 141, and includes a light blocking material for blocking light. Openings 151 are formed in parts of the light blocking layer 150. The openings 151 may be deposited or coated with a transmissive material for light transmission or may be formed as empty spaces.

The openings 151 overlap at least a part of the reflective surface 311 of the reflection portion 300. The bottom light I2 reflected through the reflection portion 300 may pass through the openings 151 and thus irradiated to the second side 112 of the transparent substrate 110.

The bottom light I2 transmitted in the second direction through the second side 112 of the transparent substrate 110 is emitted toward an object O, and then is formed as a reflective light R reflected from the object O.

The reflection portion 300 of the display device 1 may only be formed in the second light-emitting device 220. No additional reflection portion 300 may be formed in either the first light-emitting device 210 or in the third light-emitting device 230. Thus, light emitted from the first light-emitting device 210 and light emitted from the third light emitting elements 230 are formed as front light I1 and then emitted in the first direction.

For example, in the present embodiment, the reflection portions 300 may only be formed in parts of the light emitting elements 210, 220, and 230, e.g., only in the second light emitting elements 220 of the display device 1.

A portion of light from the second light emitting elements 220 is formed as the bottom light I2 and then is emitted toward the object O along the second direction. Other light from the second light emitting elements 220 and light emitted from the first and third light emitting elements 210 and 230 are formed as front lights I1 and then irradiated in the first direction, to thereby display an image.

The amount of bottom light I2 emitted in the second direction may be in a range of, for example, 5% to 25% of the amount of front light I1 emitted in the first direction. Thus, since the amount of front light I1 is significantly greater than the amount of bottom light I2 in the total amount of light emitted from the display device 1, deterioration of image quality (e.g., reduction in the amount of light in an image displayed by the front light I1) may be reduced or minimized.

The light-receiving sensors 410, 420, and 430 sense a reflective light R formed as a result of being reflected from the object O. The light-receiving sensors 410, 420, and 430 generate sense signals from the sensed reflective light R. For example, the light-receiving sensors sense the reflective light R, which corresponds to the bottom light I2 that has been emitted through the second side 112 and then returned by being reflected from an external surface, e.g., a body part.

The target O may be, for example, a part (e.g., a wrist) of the body of a wearer. The wearable device may monitor a bio-signal (e.g., heart rate) at the location where the display device 1 is worn. For example, when the wearable device where the display device 1 is worn monitors the heart rate of the wearer, the wearable device may measure the heart rate of the wearer by sensing a variation in infrared rays in the reflective light R reflected from the object O based on, for example, an infrared ray absorption difference between red blood cells in capillaries in systolic and diastolic phases of the cardiac cycle.

In the present exemplary embodiment, the reflection portion 300 is only in the second light emitting elements 230 among the plurality of light-emitting devices 210, 220, and 230. Thus, a portion of light from the second light emitting element 230 is formed as the bottom light I2. In another embodiment, the reflection portion 300 may be formed in one or more, or all, of the light emitting devices 210, 220, and 230, to thereby form the bottom lights I2 from the light emitted from the light emitting elements 210, 220, and 230.

In one embodiment, a plurality of light-receiving sensors 410, 420, and 430 may be provided. Also, one light-receiving sensor 410 may be arranged separately from another light-receiving sensor 420. In this case, the reflection portion 300 and the second light emitting element 220 may overlap a space between the light-receiving sensors 410 and 420. For example, the reflection portion 300 and the second light-emitting device 220 may be provided at an upper side of the space between the light-receiving sensors 410 and 420. Thus, the bottom light I2 reflected from the reflection portion 300 and then emitted in the second direction may be prevented from being interrupted by the light-receiving sensors 410, 420, and 430.

In the present exemplary embodiment, the reflection portion 300 and the second light-emitting device 220 are at the upper side of the space between the light-receiving sensors 410, 420, and 430. In another embodiment, the second light-emitting device 220 may overlap the light-receiving sensors 410, 420, and 430 and the reflection portion 300 may overlap the space.

Thus, in accordance with the present embodiment, a single display device having a simple structure may emit light simultaneously in different directions. Since the display device may simultaneously emit light in different directions, the thickness of a wearable display using the display device may be substantially reduced, thereby improving comfort of the user.

Figure 3:
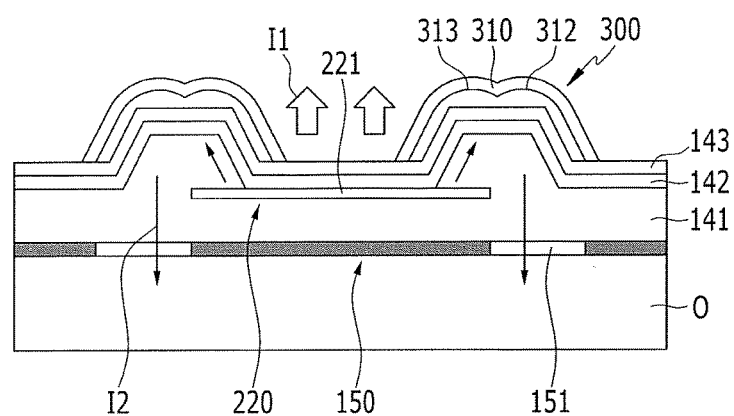
FIG. 3 illustrates another embodiment of a display device.

FIG. 3 is a partially enlarged view of another embodiment of a display device which is substantially the same as the display device in FIGS. 1 and 2, except for a reflection portion.

Referring to FIG. 3, reflective surfaces 312 and 313 are formed to reflect light emitted from a second emission element 220 in a reflection member 310 of a reflection portion 300 of display device 1. The reflective surfaces 312 and 313 include a first reflective surface 312 having a first curvature center and a first curvature, and a second reflective surface 312 connected with the first reflective surface 312 and having a second curvature center and a second curvature.

In this case, at least a pair selected from the first curvature center and the second curvature center and the first curvature and the second curvature is set to be different from each other. For example, the first reflective surface 312 and the second reflective surface 313 may be formed of different curved surfaces connected to each other. Since the reflective surfaces 312 and 313 of the reflection portion 300 are formed as a plurality of curved surfaces, light emitted from the second light emitting element 220 may be more uniformly reflected.

Figure 4:
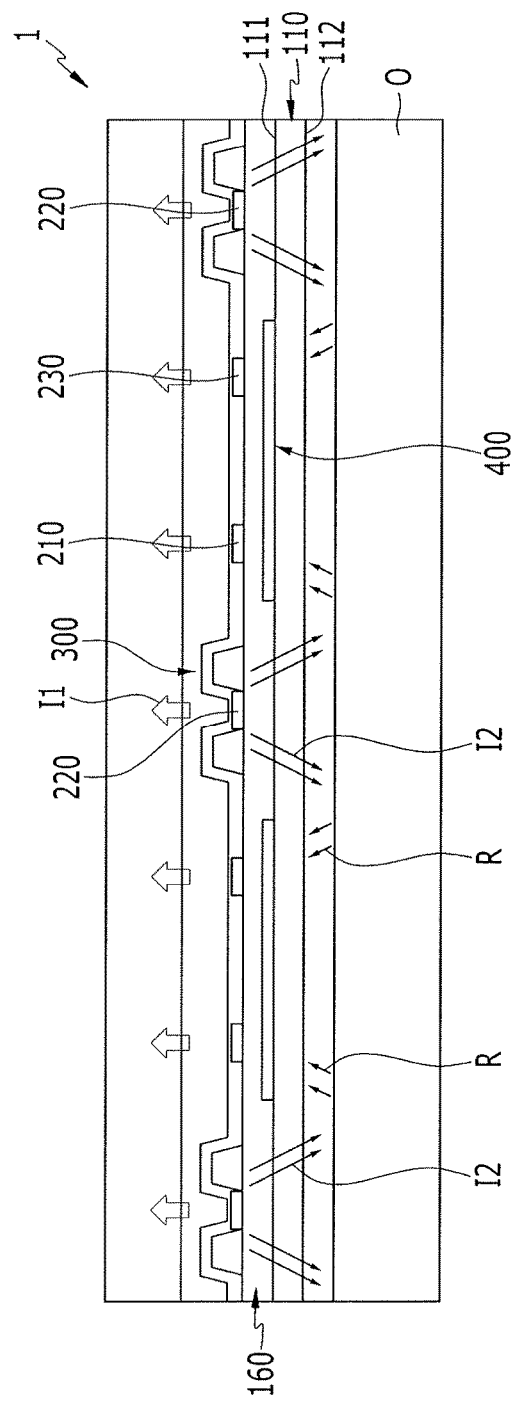
FIG. 4 illustrates another embodiment of a display device.

FIG. 4 is a cross-sectional view of another embodiment of a display device which is substantially the same as the display device in FIGS. 1 and 2, except for the alignment of light-receiving sensors 400.

Referring to FIG. 4, each light receiving sensor 400 is provided at a first side 111 of a transparent substrate 110 and includes a light-receiving sensor protection layer 160 covering the first side 111 of the transparent substrate 110. The protection layer 160 may be made of a light-transmissive material. In addition, light emitting elements 210, 220, and 230 may be above the light-receiving sensor protection layer 160. Reflective light R, generated after a bottom light I2 of the display device 1, is emitted toward an object O, passes through a second side 112 of the transparent substrate 110, and then is transmitted to the light-receiving sensor 400.

Figure 5:
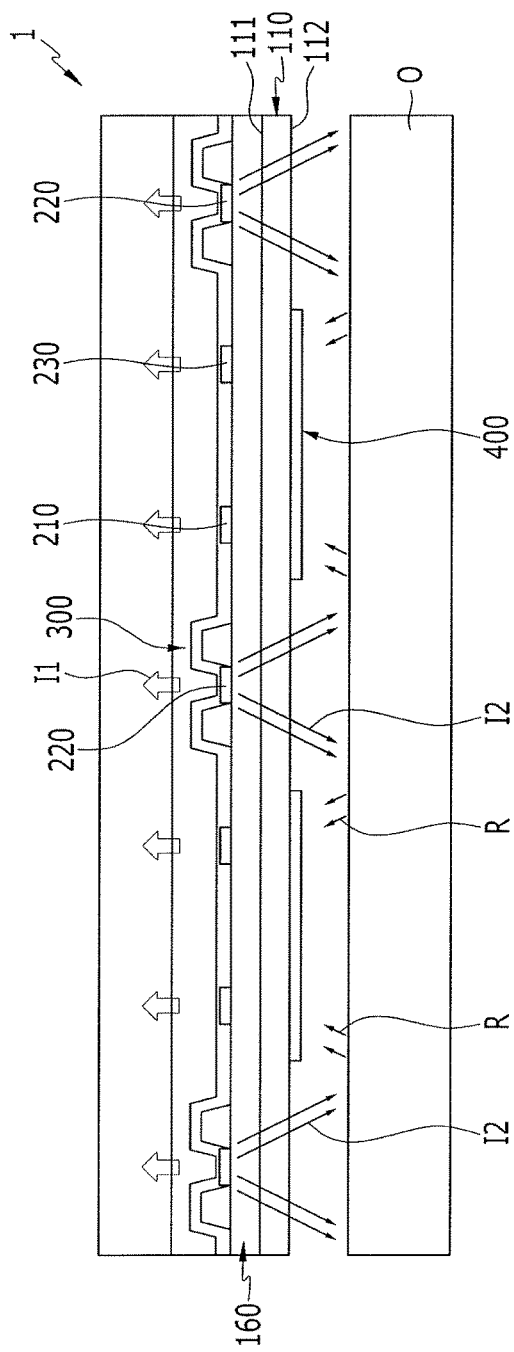
FIG. 5 illustrates another embodiment of a display device.

FIG. 5 is a cross-sectional view of another embodiment of a display device which is substantially the same as the display device in FIGS. 1 and 2, except for alignment of light-receiving sensors 400.

Referring to FIG. 5, the light-receiving sensor 400 is provided at a second side 112 of a transparent substrate 110 and includes a light-receiving sensor protection layer 160 covering the second side 112 of the transparent substrate 110. The protection layer 160 is made of a light-transmissive material. Reflective light R, generated after a bottom light I2 of the display device 1 is emitted toward an object O, passes through the light-receiving sensor protection layer 160, and then is transmitted to the light-receiving sensor 400.

Figure 6:
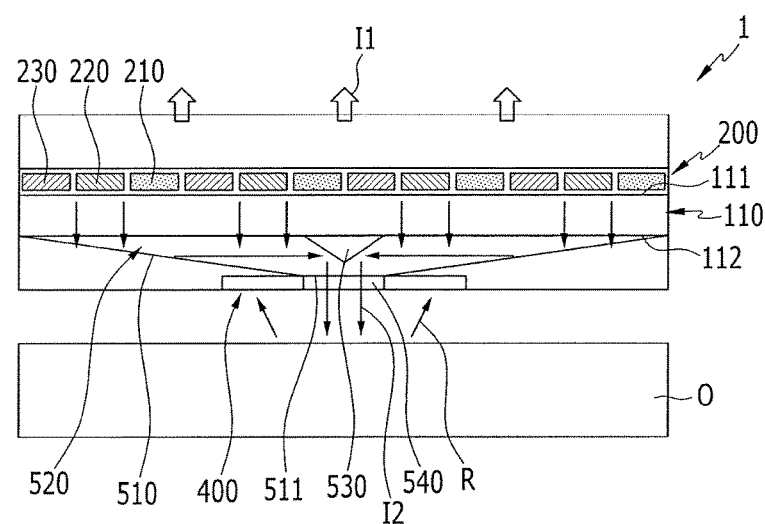
FIG. 6 illustrates another embodiment of a display device.

FIG. 6 is a cross-sectional view of another embodiment of a display device which is substantially the same as the display device in FIGS. 1 and 2, except for a configuration of collecting bottom light.

Referring to FIG. 6, the display device 1 includes a reflective plate 510, a reflective space 520, a light collecting member 520, and a shielding member 540. The reflective plate 510 covers a second side 112 of a transparent substrate 110, and an opening 511 is formed in a center of the reflective plate 510. The reflective plate 510 may be made of a highly-reflective metal material, and may be formed to gradually incline toward the center where opening 511 is formed in an edge of the reflective plate, in order to face a second direction.

The light-receiving sensor 400 is adjacent to the opening 511 of the reflective plate 510.

The reflective space 520 is between the reflective plate 510 and the transparent substrate 110. The thickness of the reflective plate 520 gradually increases toward the center of the second side 112 of the transparent substrate 110 from the edge of the second side 112. The reflective space 520 may be an empty space or may be filled with a light-transmissive material or another material.

The light collecting member 530 is in the reflective space 520 and aligned with the opening 511 of the reflective plate 510. The light collecting member 530 may be, for example, a light collecting lens that collects incident light for improving luminance.

The shielding member 540 is in the opening 511 and selectively shuts off or opens the opening 511. The shielding member 540 may be, for example, an optical switch formed based on polymer dispersed liquid crystal (PDLC) or micro electro mechanical system (MEMS).

In the present exemplary embodiment, bottom light I2 emitted in the second direction from light emitting elements 220, is reflected to the reflective space 520 from inside the reflective plate 510, and then is transmitted to the light collecting member 530. The bottom light I2 that is transmitted to the light collecting member 530 is collected by the light collecting member 530 with higher luminance, and thus may be emitted to the object O through the opening 511.

The shielding member 540 in the opening 511 selectively shuts off the opening 511, in order to selectively block the bottom light I2 emitted to outside from the display device 1.

Figure 7:
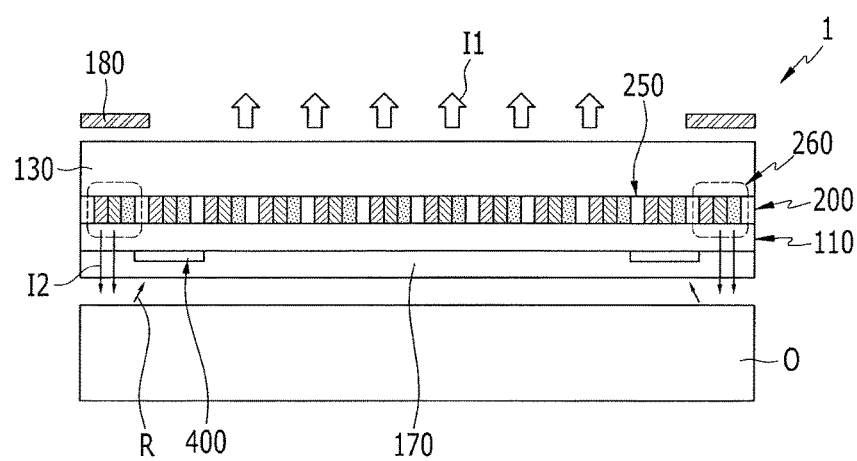
FIG. 7 illustrates another embodiment of a display device.

FIG. 7 is a cross-sectional view of another embodiment of a display device which is substantially the same as the display device in FIGS. 1 and 2, except for the configuration of light emitting elements 200.

Referring to FIG. 7, light emitting elements 200 are provided at a first side 111 of a transparent substrate 110. The light emitting elements 200 include front light emitting elements 250 to emit front light I1 in a first direction (e.g., from a front side) and bottom light emitting elements 260 to emit bottom light I2 in a second direction (e.g., from a bottom side).

The bottom light emitting elements 260 are adjacent to an edge of the transparent substrate 110. The front light emitting elements 250 are closer to a center side of the transparent substrate 110 than the bottom light emitting elements 260.

The light-receiving sensor 400 is adjacent to an edge of the second side 112 of the transparent substrate 110, and does not overlap the bottom light emitting elements 260. As a result, interference with the bottom light I2 irradiated from the bottom light emitting element 260 may be reduced or prevented.

The display device 1 also includes a light-receiving sensor protection layer 170 and a shielding member 180. The light-receiving sensor protection layer 170 covers the light-receiving sensor 400 and the second side 112 of the transparent substrate 110. The protection layer 170 may be made of a light-transmissive material.

The shielding member 180 covers the bottom light emitting elements 260 in the first direction. Thus, the bottom light emitting elements 260 may be hidden when the display device 1 is viewed from the front side.

In the display device 1, the bottom light I2 in the second direction is emitted from the bottom light emitting element 260 and, thus, passes through the transparent substrate 110 and the light-receiving sensor protection layer 170. The light is then emitted toward the object O. Further, reflective light R reflected from the object O is transmitted to the light-receiving sensor 400.

Figure 8:
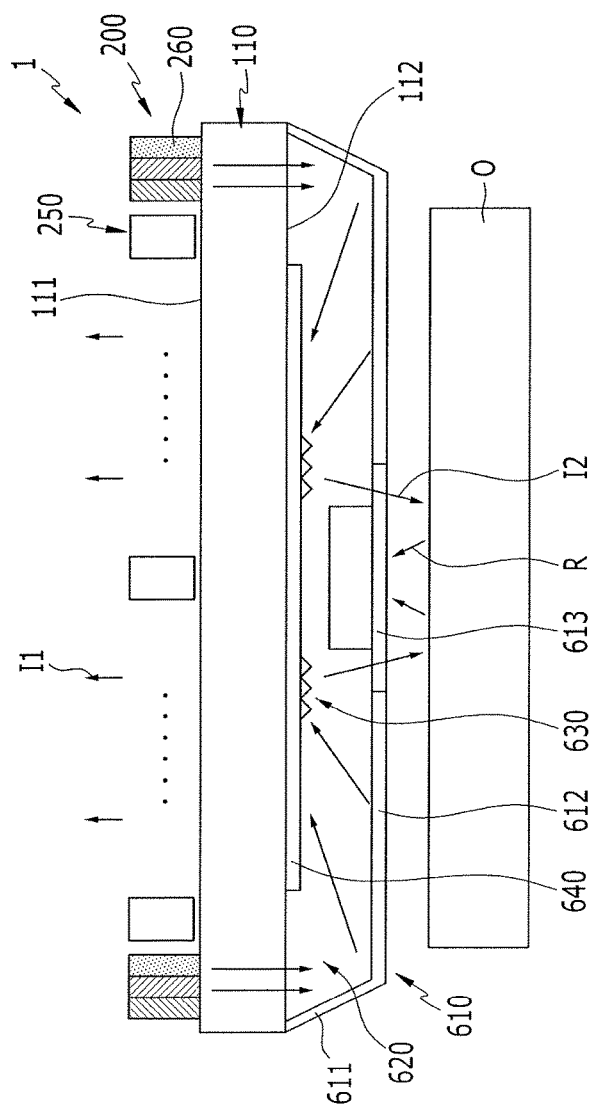
FIG. 8 illustrates another embodiment of a display device.

FIG. 8 is a cross-sectional view of another embodiment of a display device which is substantially the same as the display device in FIGS. 1 and 2, except for the configuration of collecting bottom light.

Referring to FIG. 8, light-emitting elements 200 are provided at a first side 111 of a transparent substrate 110. The light-emitted elements 200 include front light-emitting elements 250 that emit front light I1 in a first direction (e.g., a front side) and bottom light emitting elements 260 that emit bottom light I2 in a second direction (e.g., a bottom side). The bottom light emitting elements 260 are adjacent to an edge of the transparent substrate 110. The front light emitting elements 250 are closer to a center side of the transparent substrate 110 than the bottom light emitting elements 260.

The display device 1 further includes a reflective plate 610, a reflective space 620, a light collecting member 630, and an assistant plate 640. The reflective plate 610 covers a second side 112 of the transparent substrate 110, and an opening 613 is formed while penetrating a center of the reflective plate 610. The reflective plate 610 includes a first area 611 obliquely inclined toward the second direction and connected to a first area 611 at an edge side of the second side 112 and a second area 612 connected to the first area 611 and parallel to the second side 112. The opening 613 is at a center of the second region 612.

The first area 611 and the second area 612 of the reflective plate 610 may be made of, for example, a highly-reflective metal material. The reflective space is between the reflective plate 610 and the transparent substrate 110. In this case, the light-receiving sensor 400 is at in an inner side of the opening 611 in the reflective plate 610 (e.g., in the reflective space) and is adjacent to the opening 611.

The assistant plate 640 is at the second side 112 of the transparent substrate 110, and does not overlap the bottom light emitting elements 260. The assistant plate 640 may be made of, for example, the same material as the reflective plate 610.

The light collecting member 630 is on the assistant plate 640 in the reflective space 620, and is aligned with the opening 613 of the reflective plate 610. The light collecting member 630 may be, for example, a light collecting lens that collects incident light for improving luminance.

By way of summation and review, one or more embodiments provide a display device that may monitor the body of the user by emitting a portion of light from the light emitting element of the display panel toward the bottom of the display panel and receiving light reflected by the body.

Example embodiments have been disclosed herein, and although specific terms are employed, they are used and are to be interpreted in a generic and descriptive sense only and not for purpose of limitation. In some instances, as would be apparent to one of skill in the art as of the filing of the present application, features, characteristics, and/or elements described in connection with a particular embodiment may be used singly or in combination with features, characteristics, and/or elements described in connection with other embodiments unless otherwise indicated. Accordingly, it will be understood by those of skill in the art that various changes in form and details may be made without departing from the spirit and scope of the invention as set forth in the following claims.

What is claimed is:

1. A display device, comprising:
    a transparent substrate;
    a plurality of organic light emitting diodes at a first side of the transparent substrate, the organic light emitting diodes emitting light in a first direction to display an image to be viewed by a user of the display device and at least one of the organic light emitting diodes also having light emitted in a second direction, different from the first direction, the light emitted in the second direction passing through a second side of the transparent substrate; and
    a sensor configured to sense light that is emitted by the organic light emitting diodes in the second direction, exits the display device, and is then reflected to the sensor from a portion of the user's body.

2. The display device as claimed in claim 1, further comprising:
    a reflector to at least partially reflect the light emitted in the first direction to the second direction.

3. The display device as claimed in claim 2, wherein the reflector includes:
    a reflective surface that covers a portion of a light emission surface of one or more of the organic light emitting diodes, the reflective surface having a concave shape toward the first direction.

4. The display device as claimed in claim 3, further comprising: a cathode between the reflector and one or more of the organic light emitting diodes and connected to the one or more organic light emitting diodes, wherein a part of the cathode is curved in the first direction along the reflective surface of the reflector.

5. The display device as claimed in claim 3, wherein:
    the reflective surface includes a first reflective surface having a first curvature center and a first curvature and a second reflective surface having a second curvature center and a second curvature, and
    at least two of the first curvature center, the second curvature center, the first curvature, and the second curvature are different from each other.

6. The display device as claimed in claim 2, wherein:
    the reflector includes a first reflection portion and a second reflection portion, and
    the first reflection portion and the second reflection portion cover different edges of one of the organic light emitting diodes.

7. The display device as claimed in claim 2, wherein:
    the plurality of organic light emitting diodes includes first organic light emitting diodes to emit light of a first color, second organic light emitting diodes to emit light of a second color, and third organic light emitting diodes to emit light of a third color, and
    the reflector partially covers at least one of the first, second, or third organic light emitting diodes.

8. The display device as claimed in claim 2, further comprising:
    a light blocking layer between the transparent substrate and one or more of the organic light emitting diodes, wherein an opening that at least partially overlaps the reflector and through which light is to be transmitted is in the light blocking layer.

9. The display device as claimed in claim 2, wherein:
    the sensor includes a first sensor and a second sensor, and
    the reflector overlaps a space between the first and second sensors.

10. The display device as claimed in claim 1, wherein:
    the sensor is at the first side of the transparent substrate,
    a protection layer covers the sensor, and
    the organic light emitting diodes are on the protection layer.

11. The display device as claimed in claim 1, wherein:
    the sensor is at the second side of the transparent substrate, and
    a protection layer covers the sensor.

12. The display device as claimed in claim 1, further comprising:
    a reflective plate covering the second side of the transparent substrate and including an opening in a center of the reflective plate;
    a reflective space between the reflective plate and the transparent substrate; and
    a light collector in the reflective space and substantially aligned with the opening of the reflective plate.

13. The display device as claimed in claim 12, wherein:
    the reflective plate gradually inclines from an edge of the reflective plate toward the second direction closer to the center where the opening is formed, and
    a thickness of the reflective space gradually increases from an edge of the second side toward a center of the second side.

14. The display device as claimed in claim 12, wherein the sensor is adjacent to the opening.

15. The display device as claimed in claim 12, further comprising:
    a shield to selectively shut off or open the opening.

16. The display device as claimed in claim 12, wherein the reflective space includes light-transmissive material.

17. The display device as claimed in claim 12, wherein the sensor is in the reflective space and substantially aligned with the opening.

18. The display device as claimed in claim 1, wherein:
    the organic light emitting diodes include front organic light emitting diodes to emit light in the first direction and bottom organic light emitting diodes to emit light in the second direction, and
    the bottom organic light emitting diodes are adjacent to an edge of the transparent substrate.

19. The display device as claimed in claim 18, further comprising: a shield covering the bottom organic light emitting diodes in the first direction.

20. The display device as claimed in claim 18, comprising a sensor that is adjacent to the edge of the second side of the transparent substrate and does not overlap the bottom organic light emitting diodes.

21. The display device as claimed in claim 1, wherein an amount of light to be emitted in the second direction is in a range of about 5% to about 25% of an amount of light to be emitted in the first direction.

* * * * *